US011021741B2

(12) United States Patent
Wu et al.

(10) Patent No.: US 11,021,741 B2
(45) Date of Patent: Jun. 1, 2021

(54) METHODS FOR ATTACHING CELLULAR CONSTITUENTS TO A MATRIX

(71) Applicant: President and Fellows of Harvard College, Cambridge, MA (US)

(72) Inventors: Chao-ting Wu, Brookline, MA (US); Son Nguyen, West Roxbury, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 246 days.

(21) Appl. No.: 16/095,456

(22) PCT Filed: Apr. 19, 2017

(86) PCT No.: PCT/US2017/028278
§ 371 (c)(1),
(2) Date: Oct. 22, 2018

(87) PCT Pub. No.: WO2017/184682
PCT Pub. Date: Oct. 26, 2017

(65) Prior Publication Data
US 2019/0127786 A1    May 2, 2019

Related U.S. Application Data

(60) Provisional application No. 62/326,266, filed on Apr. 22, 2016.

(51) Int. Cl.
*C12Q 1/6841* (2018.01)
*C12P 19/34* (2006.01)
*C12Q 1/68* (2018.01)

(52) U.S. Cl.
CPC ............ *C12Q 1/6841* (2013.01); *C12P 19/34* (2013.01); *C12Q 1/68* (2013.01)

(58) Field of Classification Search
None
See application file for complete search history.

(56) References Cited

U.S. PATENT DOCUMENTS

2013/0084574 A1    4/2013  Dong et al.
2014/0364333 A1   12/2014  Wu et al.

FOREIGN PATENT DOCUMENTS

| CN | 101636649 A | 1/2010 |
| JP | 2001-122892 A | 5/2001 |
| JP | 2011-517555 A | 6/2011 |
| JP | 2012-514475 A | 6/2012 |
| JP | 2012-518430 A | 8/2012 |

OTHER PUBLICATIONS

Gohring et al, Biochem., vol. 36, pp. 8276-8283, published 1997.*
(Continued)

*Primary Examiner* — Robert T. Crow
(74) *Attorney, Agent, or Firm* — Banner & Witcoff, Ltd.

(57) ABSTRACT

The present invention relates to a method of covalently attaching a chromosome within a cell to a matrix including modifying a plurality of nucleotides within the chromosome to include a matrix attachment moiety wherein the chromosome contacts the matrix, and attaching the matrix attachment moiety of the plurality of nucleotides to the matrix, thereby attaching the chromosome to the matrix.

32 Claims, 3 Drawing Sheets

(56) References Cited

OTHER PUBLICATIONS

Rao et al., "A 3D Map of the Human Genome at Kilobase Resolution Reveals Principles of Chromatin Looping," Cell, vol. 159, No. 7, pp. 1665-1680 (Dec. 18, 2014).
Beliveau, et al. Single-molecule super-resolution imaging of chromosomes and in situ haplotype visualization using Oligopaint Fish probes. Nat Commun. 2015; 6:7147; Abstract, p. 3 [according to the posted document], Fig 1 and its legend; p. 4, Fig 2 and its legend; p. 6, Fig 3 and its legend.
Chen, et al. Expansion microscopy. Science 2015, 347(6221): 543-548; Abstract, p. 544, col. 1 and Fig. 1 and its legend; Supplementary Materials, p. 3, 4.
Yaroslavsky, et al. Fluorescence imaging of single-copy DNA sequences within the human genome using PNA-padlock directed probe assembly. Chemistry & biology 2013, 20(3):445-453; Abstract, p. 447, Figure 1 and its legend; p. 448, Table 1.
Beliveau, Brian J. et al., "Versatile design and synthesis platform for visualizing genomes with Oligopaint FISH probes", National Academy of Sciences, vol. 109, No. 52, Dec. 11, 2012, pp. 21301-21306.
Beliveau, Brian J. et al., Visualizing Genomes with Oligopaint Fish Probes: In: "Current Protocols in Molecular Biology", Jan. 6, 2014, Wiley, New York, NY.
Chen, Fei et al., "Nanoscale imaging of RNA 1-15 with expansion microscopy", Nature Methods, vol. 13, No. 8, Aug. 1, 2016, pp. 679-684.
Nir, Guy et al., "Walking along chromosomes with super-resolution imaging, contact maps, and integrative modeling", 'PLOS Genetics, vol. 14, No. 12, Dec. 26, 2018 (Dec. 26, 2018).
Chozinski et al., "Expansion microscopy with conventional antibodies and fluorescent proteins," Nature Methods, vol. 13, No. 6, pp. 485-488 (Apr. 11, 2016).

\* cited by examiner

METHODS FOR ATTACHING CELLULAR CONSTITUENTS TO A MATRIX

RELATED APPLICATIONS

This application is a National Stage Application under 35 U.S.C. 371 of co-pending PCT application PCT/US17/28278 designating the United States and filed Apr. 19, 2017; which claims the benefit of U.S. provisional application No. 62/326,266 filed on Apr. 22, 2016 each of which are hereby incorporated by reference in their entireties.

STATEMENT OF GOVERNMENT INTERESTS

This invention was made with government support under grant number 1 RO1 GM085169 awarded by National Institutes of Health and grant number 5DP1GM106412 awarded by National Institutes of Health. The government has certain rights in the invention.

FIELD

The present invention relates in general to the attachment of cellular constituents to a matrix within a cell.

BACKGROUND

Fluorescence in situ hybridization (FISH) is a powerful technology wherein nucleic acids are targeted by fluorescently labeled probes and then visualized via microscopy. FISH is a single-cell assay, making it especially powerful for the detection of rare events that might be otherwise lost in mixed or asynchronous populations of cells. In addition, because FISH is applied to fixed cell or tissue samples, it can reveal the positioning of chromosomes relative to nuclear, cytoplasmic, and even tissue structures, especially when applied in conjunction with immunofluorescent targeting of cellular components. FISH can also be used to visualize RNA, making it possible for researchers to simultaneously assess gene expression, chromosome position, and protein localization.

SUMMARY

The present disclosure provides methods of attaching cellular constituents to a matrix introduced into a cell. The disclosure provides a method of covalently attaching a chromosome within a cell to a matrix including modifying a plurality of nucleotides within the chromosome to include a matrix attachment moiety wherein the chromosome contacts the matrix, and attaching the matrix attachment moiety of the plurality of nucleotides to the matrix, thereby attaching the chromosome to the matrix. The disclosure provides a method of modeling structure of a chromosome in a cell including hybridizing to the chromosome a plurality of oligonucleotides, wherein the chromosome contacts a matrix within the cell, and attaching the plurality of oligonucleotides to the matrix, wherein the plurality of oligonucleotides attached to the matrix represents the structure of the chromosome in the cell. The plurality of oligonucleotides may be oligopaints as described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawing in which:

FIG. 3A-E are directed to experiments demonstrating that acrydite modified Oligopaints allow tethering of Oligopaint to ExM gel matrix. FIG. 3B-3E depict PGP1F cells stained with ~20,000 Oligopaints (green) targeting 2.1 Mb region on q arm of Chromosome 19 (9.2 probes/Kb) in ExM gel. Non-modified Oligopaints are shown in FIGS. 3B-3C. Acrydite modified Oligopaints are shown in FIGS. 3D-3E. Acrydite modified Oligopaints remain attached to Expansion gel after Oligopaint removal by treatment with 70% formamide at 73 degrees (FIG. 3E), while non-modified Oligopaints do not (FIG. 3C). Scale bar=10 microns.

DETAILED DESCRIPTION

Terms and symbols of nucleic acid chemistry, biochemistry, genetics, and molecular biology used herein follow those of standard treatises and texts in the field, e.g., Komberg and Baker, *DNA Replication*, Second Edition (W.H. Freeman, New York, 1992); Lehninger, *Biochemistry*, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

The disclosure provides methods of attaching cellular constituents to a matrix within a cell. According to one aspect, methods described herein are directed to immobilizing, through covalent linkage or otherwise, naturally occurring nucleic acids, such as chromosomes or RNA, within their native environment, such as within a cell or within a tissue sample. The three dimensional nucleic acid matrix can be generated in situ in a cell or tissue sample to preserve the naturally occurring nucleic acid sequence diversity (such as DNA and RNA) and spatial orientation in cells, tissues or any other complex biomaterial. According to this aspect, the location of nucleic acids and their relative position is identified as a three dimensional structure, such as within sub-cellular compartments, within cells, within tissues, as three dimensional nucleic acid assemblies, as three dimensional nucleic acid material, etc.

The disclosure provides a method of covalently attaching a chromosome within a cell to a matrix including modifying a plurality of nucleotides within the chromosome to include a matrix attachment moiety wherein the chromosome contacts the matrix, and attaching the matrix attachment moiety of the plurality of nucleotides to the matrix, thereby attaching the chromosome to the matrix. The disclosure provides that a matrix-forming material is introduced into the cell and forms the matrix contacting the chromosome. The disclosure provides that the matrix may be expanded and additional nucleotides within the chromosome are modified to include a matrix attachment moiety and the matrix attachment moiety is attached to the matrix. Although a single expansion may be sufficient, the disclosure provides that the matrix is expanded one or more additional times, i.e. the matrix may be repeatedly expanded, and additional nucleotides within the chromosome are modified to include a matrix attachment moiety and the matrix attachment moiety is attached to the matrix. The disclosure provides that the matrix-forming material is polymerized to form the matrix. The disclosure provides that the matrix-forming material is crosslinked to form the matrix. The disclosure provides that the plurality of nucleotides are chemically modified to include the matrix attachment moiety. The disclosure provides that the plurality of nucleotides are chemically modified to include a binding site for a matrix attachment moiety directly or through a linker, and the matrix attachment moiety or the linker is bound to the binding site. The disclosure provides that the plurality of nucleotides are modified by being cleaved from an adjacent nucleotide to produce one or more free end terminal nucleotides, and wherein a nucleotide including a matrix attachment moiety is connected directly or as part of an oligonucleotide to the one or more free end terminal nucleotides, and the matrix attachment moiety is attached to the matrix. The disclosure provides that the free end terminal nucleotides are processed to allow attachment of the nucleotide including a matrix attachment moiety or the oligonucleotide including the nucleotide including a matrix attachment moiety. The disclosure provides that the free end terminal nucleotides are processed to create blunt ends to allow attachment of the nucleotide including a matrix attachment moiety or the oligonucleotide including the nucleotide including a matrix attachment moiety. The disclosure provides that the free end terminal nucleotides are processed to create overhangs to allow attachment of the nucleotide including a matrix attachment moiety or the oligonucleotide including the nucleotide including a matrix attachment moiety. The disclosure provides that the chromosomal DNA is cleaved by a restriction enzyme, a DNase, a single strand cutter, a double strand cutter, or irradiation to create a plurality single stranded or double stranded breaks or gaps. The disclosure provides that the nucleotide including a matrix attachment moiety is ligated directly or via an oligonucleotide to the one or more free end terminal nucleotides. The disclosure provides that the nucleotide including a matrix attachment moiety is extended from the one or more free end terminal nucleotides. The disclosure provides that one or more modified nucleotides are added to a terminal nucleotide using a polymerase, attaching a matrix attachment moiety to the one or more modified nucleotides, and attaching the matrix attachment moiety to the matrix. The disclosure provides that one or more nucleotides are added to a terminal nucleotide using a polymerase, wherein the one or more nucleotides are chemically modified to include a binding site for a matrix attachment moiety directly or through a linker, and the matrix attachment moiety or the linker is bound to the binding site, and the matrix attachment moiety is attached to the matrix. The disclosure provides that the matrix attachment moiety is one or more of amine, amine reactive groups, acrydite, an acrydite modified entity, alkyne, biotin, azide, thiol, and a thiol-modified entity and entities suitable for click chemistry techniques. The disclosure provides that the matrix material is expanded in three dimensions creating breaks in chromosomal DNA producing one or more additional free end terminal nucleotides. The disclosure provides that the matrix is one or more of polyacrylamide, cellulose, alginate, polyamide, crosslinked agarose, cross-linked dextran, cross-linked polyethylene glycol.

The disclosure provides that for a method of modeling structure of a chromosome in a cell including hybridizing to the chromosome a plurality of oligonucleotides, wherein the chromosome contacts a matrix within the cell, and attaching the plurality of oligonucleotides to the matrix, wherein the plurality of oligonucleotides attached to the matrix represents the structure of the chromosome in the cell, as the oligonucleotides are hybridized to the chromosome. The plurality of oligonucleotides may be probes, such as oligopaints or ISH or FISH probes and may be any suitable length, as described herein, such as short probes being about 5 nucleotides in length to 1 kb or 2 kn or 3 kn or longer. Suitable probes may be attached to a matrix at one or more or a plurality of locations along the probe to simulate the sequence of the chromosome. The disclosure provides that a matrix-forming material is introduced into the cell and forms the matrix contacting the chromosome. The disclosure provides that the matrix may be expanded and additional oligonucleotides are hybridized to the chromosome and attached to the matrix. Though a single expansion may be sufficient, the disclosure provides that the matrix may be expanded one or more times, i.e. may be repeatedly expanded, and additional oligonucleotides are hybridized to the chromosome and attached to the matrix. The disclosure provides that the matrix-forming material is polymerized to form the matrix. The disclosure provides that the matrix-forming material is crosslinked to form the matrix. The disclosure provides removing the chromosome from the material, wherein the plurality of oligonucleotides attached to the matrix material represents the structure of the chromosome in the cell, as the oligonucleotides were hybridized to the chromosome and are attached to the matrix. The disclosure provides that the plurality of oligonucleotides include a matrix attachment moiety that is attached to the matrix. The disclosure provides that the plurality of oligonucleotides includes a matrix attachment moiety or one or more or a plurality of matrix attachment moieties, that is attached to the matrix and wherein the plurality of oligonucleotides includes DNA attachment moieties and the DNA attachment moieties are attached to chromosomal DNA. The disclosure provides that the plurality of oligonucleotides is chemically modified to include a matrix attachment moiety and the matrix attachment moiety is attached to the matrix. The disclosure provides that the plurality of oligonucleotides include a secondary probe hybridization site and a secondary probe including a matrix attachment moiety is hybridized to the secondary probe hybridization site and the matrix attachment moiety is attached to the matrix. The disclosure provides that the plurality of oligonucleotides includes a plurality of secondary probe hybridization sites and secondary probes including a matrix attachment moiety is hybridized to the plurality of secondary probe hybridization sites and the matrix attachment moiety is attached to the matrix.

Figure 1:
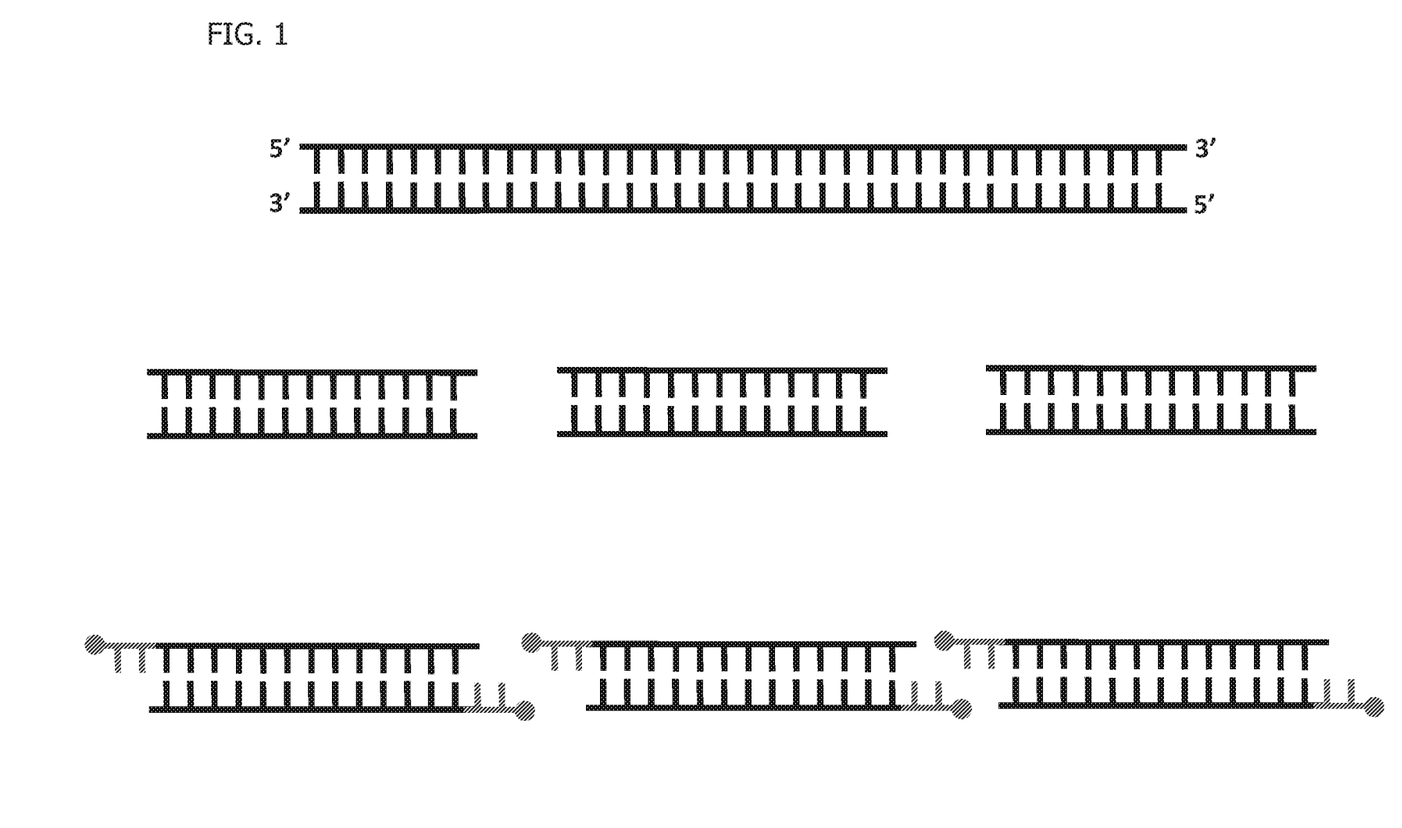
FIG. 1 is a schematic depicting the cleaving of a nucleic acid and the addition of a matrix attachment moiety to free end terminal nucleotides.

With reference to FIG. 1, a chromosome is depicted as a double stranded nucleic acid within a cell. The cell is formaldehyde-treated for fixation or provided with a matrix forming material and matrix is formed within the cell contacting the chromosome, for example surrounding the chromosome in a manner to immobilize the chromosome and retain its three-dimensional shape and relative position within the cell. The chromosome is fragmented using a fragmenting method to produce fragments having free end terminal nucleotides. The ends may be processed as needed to produce blunt ends or overhangs. Oligonucleotides with an attachment moiety, such as an acrydite moiety, are ligated to the free end terminal nucleotides and are then attached to the matrix. The matrix may be expanded one or more times. Expandable matrix materials and methods of expanding a matrix are known to those of skill in the art.

With respect to the methods described above and herein, the following sections are provided for exemplary aspects of certain features of the methods.

Cellular Constituents

The present disclosure provides for the attachment of cellular constituents to a matrix within a cell. Exemplary cellular constituents include chromosomes, proteins, RNA and the like. As used herein, the term "chromosome" refers to the support for the genes carrying heredity in a living cell, including DNA, protein, RNA and other associated factors. There exists a conventional international system for identifying and numbering the chromosomes of the human genome. The size of an individual chromosome may vary within a multi-chromosomal genome and from one genome to another. A chromosome can be obtained from any species. A chromosome can be obtained from an adult subject, a juvenile subject, an infant subject, from an unborn subject (e.g., from a fetus, e.g., via prenatal test such as amniocentesis, chorionic villus sampling, and the like or directly from the fetus, e.g., during a fetal surgery) from a biological sample (e.g., a biological tissue, fluid or cells (e.g., sputum, blood, blood cells, tissue or fine needle biopsy samples, urine, cerebrospinal fluid, peritoneal fluid, and pleural fluid, or cells therefrom) or from a cell culture sample (e.g., primary cells, immortalized cells, partially immortalized cells or the like). In certain exemplary embodiments, one or more chromosomes can be obtained from one or more genera including, but not limited to, *Homo, Drosophila, Caenorhabiditis, Danio, Cyprinus, Equus, Canis, Ovis, Ocorynchus, Salmo, Bos, Sus, Gallus, Solanum, Triticum, Oryza, Zea, Hordeum, Musa, Avena, Populus, Brassica, Saccharum* and the like.

Matrix Materials and Making a Matrix within a Cell

The disclosure provides for the use of a matrix within a cell formed from one or more matrix-forming materials for the attachment of cellular constituents to the matrix. Cellular constituents, such as chromosomes, are covalently attached to the matrix to preserve their spatial orientation in the X, Y and Z axes within the matrix. An exemplary matrix material may be a semi-solid medium that can be made from or can be polyacrylamide, cellulose, alginate, polyamide, cross-linked agarose, cross-linked dextran, cross-linked polyethylene glycol and the like. It is to be understood that the matrix may be formed from monomers or oligomers that are polymerized to form the matrix or from polymers or oligomers that are crosslinked to form the matrix or both. Methods for making three dimensional matrices within a cell are known to those of skill in the art and include introducing one or more components of matrix forming materials into a cell or tissue sample and forming the matrix within the cell. The matrix forming materials can form a matrix by polymerization and/or crosslinking of the matrix forming materials using methods specific for the matrix forming materials and methods, reagents and conditions known to those of skill in the art.

The disclosure provides that an exemplary three dimensional matrix is porous, i.e. to the extent that desired reagents or materials or probes can diffuse or otherwise move through the matrix to contact nucleic acids. Porosity can result from polymerization and/or crosslinking of molecules used to make the matrix material or from using molecular sieves. The diffusion property within the gel matrix is largely a function of the pore size. The porosity is controlled by changing the cross-linking density, the chain lengths and the percentage of co-polymerized branching monomers according to methods known to those of skill in the art.

According to one aspect, the three dimensional matrix material is chemically inert and thermally stable to allow for various reaction conditions and reaction temperatures, such as are desirable for fluorescence in situ hybridization. According to one aspect, the three dimensional matrix material is optically transparent. According to one aspect, the three dimensional matrix material is optically transparent to allow for three dimensional imaging techniques known to those of skill in the art. According to one aspect, the material used to form the matrix is compatible with a wide range of biological and non-biological specimens in situ so as to avoid extracting the nucleic acid molecules away from their native environment. According to one aspect, the matrix may be expandable in the X, Y and Z axes, i.e. is expandable in three dimensions. According to one aspect, the matrix is expandable in each direction uniformly.

According to one aspect, a matrix-forming material can be introduced into a cell. The cells are fixed with formaldehyde and then immersed in ethanol to disrupt the lipid membrane. The matrix forming reagents are added to the sample and are allowed to permeate throughout the cell. A polymerization inducing catalyst, UV or functional cross-linkers are then added to allow the formation of a gel matrix. The unincorporated material is washed out and any remaining functionally reactive group is quenched. Exemplary cells include any cell, human or otherwise, including diseased cells or healthy cells. Certain cells include human cells, non-human cells, human stem cells, mouse stem cells, primary cell lines, immortalized cell lines, primary and immortalized fibroblasts, HeLa cells and neurons.

Matrix Attachment Moieties or Linkers

The disclosure provides for the use of one or more matrix attachment moieties or linkers on a nucleic acid, such as a chromosome, to attach the nucleic acid to a matrix within the cell. As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in Molecular Biology of the Cell, 3d edition, Garland Publishing, 1994, incorporated herein by reference in its entirety for all purposes. A matrix attachment moiety is one that can attach to a matrix whether through covalent linkage to a site, atom or moiety on the matrix or through noncovalent binding with a site, atom or moiety on the matrix. One of skill will readily identify a suitable matrix attachment moiety that can be used to attach a nucleic acid such as DNA or RNA to a particular matrix material.

One or more nucleotides of an existing nucleic acid, such as a chromosome or portion, fragment or section thereof, or a nucleotide added to an existing nucleic acid, such as a chromosome or portion, fragment or section thereof, may be modified to include a matrix attachment moiety. One or more nucleotides including a matrix attachment moiety may be added to an existing nucleic acid, such as a chromosome or portion, fragment or section thereof. The matrix attachment moiety may be covalently attached to the matrix within the cell, covalently cross-linked, copolymerized with or otherwise non-covalently bound to the matrix. A matrix attachment moiety may be activatable. As used herein, the term "activatable" refers to a matrix attachment moiety that is inert (i.e., does not bind a target) until activated (e.g., by exposure of the activatable matrix attachment moiety to light, heat, one or more chemical compounds or the like).

The matrix attachment moiety can react with a cross-linker. The matrix attachment moiety can be part of a ligand-ligand binding pair. An exemplary matrix attachment moiety includes an amine, amine reactive groups, acrydite, an acrydite modified entity, alkyne, biotin, azide, thiol, and a thiol-modified entity and entities suitable for click chemistry techniques. Biotin, or a derivative thereof, may be used as a matrix attachment moiety when the matrix includes an avidin/streptavidin derivative or an anti-biotin antibody (e.g., a detectably labelled antibody). Digoxigenin may be used as a matrix attachment moiety and subsequently bound by an anti-digoxigenin antibody attached to the matrix. An aminoallyl-dUTP residue may be incorporated into an oligonucleotide and subsequently coupled to an N-hydroxy succinimide which may be incorporated into the matrix. In general, any member of a conjugate pair or reactive pair may be used to attach a nucleotide, whether in an oligonucleotide or a chromosome, to a matrix.

Matrix attachment moieties include chemical cross-linking agents. Cross-linking agents typically contain at least two reactive groups that are reactive towards numerous groups, including, but not limited to, sulfhydryls and amines, and create chemical covalent bonds between two or more molecules. Matrix attachment moieties include cross-linking agents such as primary amines, carboxyls, sulfhydryls, carbohydrates and carboxylic acids. Protein molecules have many of these functional groups and therefore proteins and peptides can be readily conjugated using cross-linking agents. Cross-linking agents are well known in the art and are commercially available (Thermo Scientific (Rockford, Ill.)). In the case of crosslinking, the matrix attachment moiety may be cross-linked to modified dNTP or dUTP or both. Suitable exemplary cross-linker reactive groups include imidoester (DMP), succinimide ester (NHS), maleimide (Sulfo-SMCC), carbodiimide (DCC, EDC) and phenyl azide. Cross-linkers within the scope of the present disclosure may include a spacer moiety. Such spacer moieties may be functionalized. Such spacer moieties may be chemically stable. Suitable exemplary spacer moieties include polyethylene glycol, carbon spacers, photo-cleavable spacers and other spacers known to those of skill in the art and the like.

Detectable Labels

The disclosure provides for the use of detectable labels which may be attached to probes as described herein which may be hybridized to a cellular constituent such as a chromosome. Detectable labels or moieties are known to those of skill in the art. As used herein, the term "detectable label" refers to a label that can be used to identify a target (e.g., a factor associated with a nucleic acid sequence of interest, a chromosome or a sub-chromosomal region). Typically, a detectable label is attached to the 3'- or 5'-end of a polynucleotide. Alternatively, a detectable label is attached to an internal portion of an oligonucleotide. Detectable labels may vary widely in size and compositions; the following references provide guidance for selecting oligonucleotide tags appropriate for particular embodiments: Brenner, U.S. Pat. No. 5,635,400; Brenner et al., Proc. Natl. Acad. Sci., 97: 1665; Shoemaker et al. (1996) Nature Genetics, 14:450; Morris et al., EP Patent Pub. 0799897A1; Wallace, U.S. Pat. No. 5,981,179; and the like.

Examples of detectable moieties include various radioactive moieties, enzymes, prosthetic groups, fluorescent markers, luminescent markers, bioluminescent markers, metal particles, protein-protein binding pairs, protein-antibody binding pairs and the like. Examples of fluorescent moieties include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, cyanines, dansyl chloride, phycocyanin, phycoerythrin and the like. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorinidases, phosphatases, peroxidases, cholinesterases and the like. Identifiable markers also include radioactive compounds such as $^{125}I$, $^{35}S$, $^{14}C$, or $^{3}H$. Identifiable markers are commercially available from a variety of sources.

Fluorescent labels and their attachment to nucleotides and/or oligonucleotides are described in many reviews, including Haugland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); and Wetmur, Critical Reviews in Biochemistry and Molecular Biology, 26:227-259 (1991). Particular methodologies applicable to the invention are disclosed in the following sample of references: U.S. Pat. Nos. 4,757,141, 5,151,507 and 5,091,519. In one aspect, one or more fluorescent dyes are used as labels for labeled target sequences, e.g., as disclosed by U.S. Pat. No. 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); Lee et al.; U.S. Pat. No. 5,066,580 (xanthine dyes); U.S. Pat. No. 5,688,648 (energy transfer dyes); and the like. Labeling can also be carried out with quantum dots, as disclosed in the following patents and patent publications: U.S. Pat. Nos. 6,322,901, 6,576,291, 6,423,551, 6,251,303, 6,319,426, 6,426,513, 6,444,143, 5,990,479, 6,207,392, 2002/0045045 and 2003/0017264. As used herein, the term "fluorescent label" includes a signaling moiety that conveys information through the fluorescent absorption and/or emission properties of one or more molecules. Such fluorescent properties include fluorescence intensity, fluorescence lifetime, emission spectrum characteristics, energy transfer, and the like.

Detection method(s) used will depend on the particular detectable labels used in the reactive labels, retrievable labels and/or detectable labels. In certain exemplary embodiments, target nucleic acids such as chromosomes and sub-chromosomal regions of chromosomes during various phases of the cell cycle including, but not limited to, interphase, preprophase, prophase, prometaphase, metaphase, anaphase, telophase and cytokinesis, having one or more reactive labels, retrievable labels, or detectable labels bound thereto by way of the probes described herein may be selected for and/or screened for using a microscope, a spectrophotometer, a tube luminometer or plate luminometer, x-ray film, a scintillator, a fluorescence activated cell sorting (FACS) apparatus, a microfluidics apparatus or the like.

When fluorescently labeled targeting moieties, retrievable moieties, or detectable labels are used, fluorescence photomicroscopy can be used to detect and record the results of in situ hybridization using routine methods known in the art. Alternatively, digital (computer implemented) fluorescence microscopy with image-processing capability may be used. Two well-known systems for imaging FISH of chromosomes having multiple colored labels bound thereto include multiplex-FISH (M-FISH) and spectral karyotyping (SKY). See Schrock et al. (1996) *Science* 273:494; Roberts et al. (1999) *Genes Chrom. Cancer* 25:241; Fransz et al. (2002) *Proc. Natl. Acad. Sci. USA* 99:14584; Bayani et al. (2004) *Curr. Protocol. Cell Biol.* 22.5.1-22.5.25; Danilova et al. (2008) *Chromosoma* 117:345; U.S. Pat. No. 6,066,459; and FISH TAG™ DNA Multicolor Kit instructions (Molecular probes) for a review of methods for painting chromosomes and detecting painted chromosomes.

In certain exemplary embodiments, images of fluorescently labeled chromosomes are detected and recorded using a computerized imaging system such as the Applied Imaging Corporation CytoVision System (Applied Imaging Corporation, Santa Clara, Calif.) with modifications (e.g., software, Chroma 84000 filter set, and an enhanced filter wheel). Other suitable systems include a computerized imaging system using a cooled CCD camera (Photometrics, NU200 series equipped with Kodak KAF 1400 CCD) coupled to a Zeiss Axiophot microscope, with images processed as described by Ried et al. (1992) *Proc. Natl. Acad. Sci. USA* 89:1388). Other suitable imaging and analysis systems are described by Schrock et al., supra; and Speicher et al., supra.

Nucleotides and Modified Nucleotides

The present disclosure provides for the modification of nucleotides to include a matrix attachment moiety, or for modified nucleotides including a site for attachment of a matrix attachment moiety or for addition of nucleotides or modified nucleotides to a free end or terminal nucleotide. The terms "nucleic acid," "nucleic acid molecule," "nucleic acid sequence," "nucleic acid fragment," "oligonucleotide" and "polynucleotide" are used interchangeably and are intended to include, but not limited to, a polymeric form of nucleotides that may have various lengths, either deoxyribonucleotides or ribonucleotides, or analogs thereof. The labeled probes described herein may include or be a "nucleic acid," "nucleic acid molecule," "nucleic acid sequence," "nucleic acid fragment," "oligonucleotide" or "polynucleotide." Oligonucleotides or polynucleotides useful in the methods described herein may comprise natural nucleic acid sequences and variants thereof, artificial nucleic acid sequences, or a combination of such sequences. Oligonucleotides or polynucleotides may be single stranded or double stranded.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS).

In certain exemplary embodiments, nucleotide analogs or derivatives will be used, such as nucleosides or nucleotides having protecting groups on either the base portion or sugar portion of the molecule, or having attached or incorporated labels, or isosteric replacements which result in monomers that behave in either a synthetic or physiological environment in a manner similar to the parent monomer. The nucleotides can have a protecting group which is linked to, and masks, a reactive group on the nucleotide. A matrix attachment moiety can be added to a reactive site, or a matrix attachment moiety can be present on a nucleotide but in an inactive or blocked state by a protective group. Removal of the protective group can activate the matrix attachment moiety for attachment to a matrix. A variety of protecting groups are useful in the invention and can be selected. According to one aspect, self-avoiding nucleotides can be used to make probes. Self-avoiding nucleotides are those which are capable of base pairing with natural nucleotides, but not with themselves. Self-avoiding nucleotides are known to those of skill in the art and are described in Hoshika, et al, *Angew. Chem. Int. Ed.* 2010, 49, pp. 5554-5557 and Hoshika et al., *Nucleic Acids Research* (2008) hereby incorporated by reference in their entireties.

Hybridization Probes and Oligopaints

The present disclosure provides for the use of hybridization probes, such as Oligopaints, to hybridize to a cellular constituent, such as a chromosome, and wherein the hybridization probe includes a matrix attachment moiety and may be attached to a matrix. A matrix attachment moiety may be directly or indirectly attached or conjugated to a nucleotide or nucleic acid or probe or Oligopaint as described herein.

In general, an oligopaint includes a complementary nucleic acid sequence that is complementary to a target oligonucleotide sequence, such as a portion of a DNA sequence, or a particular chromosome or sub-chromosomal region of a particular chromosome. The complementary nucleic acid sequence may be said to have genomic homology insofar as the oligopaint is intended to hybridize with a complementary genomic nucleic acid sequence. The complementary nucleic acid sequence may be between 15 to 50 or between 32 to 42 bases in length. The complementary nucleic acid sequence may by any nucleic acid sequence and may be a DNA sequence, an RNA sequence (such as a guide RNA sequence as is understood with CRISPR systems) or a DNA/RNA hybrid sequence. The oligopaint may also include a nongenomic nucleic acid sequence or region upstream of the complementary nucleic acid sequence which may be referred to as a "Mainstreet" sequence. The oligopaint may also include a nongenomic nucleic acid sequence or region downstream of the complementary nucleic acid sequence which may be referred to as a "Backstreet" sequence. The oligopaint may include both a first nongenomic nucleic acid sequence or region upstream of the complementary nucleic acid sequence ("Mainstreet") and a second nongenomic nucleic acid sequence or region downstream of the complementary nucleic acid sequence ("Backstreet"). In this manner the complementary or genomic nucleic acid sequence may be flanked by a Mainstreet sequence and a Backstreet sequence. While the purpose of the complementary or genomic nucleic acid sequence is to hybridize with a target genomic nucleic acid sequence, the Mainstreet and Backstreet sequences may be used to carry functional moieties. The functional moieties may be directly attached to the Mainstreet or Backstreet sequences or they may be indirectly attached to the Mainstreet or Backstreet sequences. For example, a functional moiety may be indirectly attached insofar as the functional moiety is directly attached to a first nongenomic nucleic acid sequence probe which is complementary to a portion of the nongenomic Mainstreet or Backstreet sequences. In this manner, the first nongenomic nucleic acid sequence probe hybridizes to the complementary portion of the nongenomic Mainstreet or Backstreet sequences.

In situ hybridization methods using probes described herein can be performed on a variety of biological or clinical samples, in cells that are in any (or all) stage(s) of the cell cycle (e.g., mitosis, meiosis, interphase, G0, G1, S and/or G2). Examples include all types of cell culture, animal or plant tissue, peripheral blood lymphocytes, buccal smears, touch preparations prepared from uncultured primary tumors, cancer cells, bone marrow, cells obtained from biopsy or cells in bodily fluids (e.g., blood, urine, sputum and the like), cells from amniotic fluid, cells from maternal blood (e.g., fetal cells), cells from testis and ovary, and the like. Samples are prepared for assays of the invention using conventional techniques, which typically depend on the source from which a sample or specimen is taken. These examples are not to be construed as limiting the sample types applicable to the methods and/or compositions described herein.

The disclosure provides multiple chromosome-specific probes, which include matrix attachment moieties or linkers, for attachment to a matrix. Such probes may also include one or more detectable moieties. Methods according to the present disclosure include any methods known to those of skill in the art where nucleic acid probes are used to hybridize to a nucleic acid, such as a double stranded DNA where a portion of the double stranded DNA has separated into two separate strands, i.e. a first strand and a complementary strand. It is to be understood that reference to a first strand and a complementary strand is relative when separating double stranded nucleic acids. That is, either strand can be the first strand or the complementary strand. Selecting one strand as the first strand makes the remaining strand the complementary strand.

One exemplary method where the labeled probes described herein have particular utility include fluorescent in situ hybridization or FISH which is a cytogenetic technique that is used to detect and localize the presence or absence of specific DNA sequences on chromosomes. FISH uses fluorescent probes that bind to only those parts of the chromosome with which they show a high degree of sequence complementarity. Fluorescence microscopy can be used to find out where the fluorescent probe is bound to the chromosomes. FISH is often used for finding specific features in DNA for use in genetic counseling, medicine, and species identification. FISH can also be used to detect and localize specific RNA targets (mRNA, lncRNA and miRNA) in cells, circulating tumor cells, and tissue samples. In this context, it can help define the spatial-temporal patterns of gene expression within cells and tissues. Exemplary FISH methods are known to those of skill in the art and are readily available in the published literature.

Hybridization of the probes including a matrix attachment moiety or linker to target chromosomes sequences can be accomplished by standard in situ hybridization (ISH) techniques (see, e.g., Gall and Pardue (1981) *Meth. Enzymol.* 21:470; Henderson (1982) *Int. Review of Cytology* 76:1). Generally, ISH comprises the following major steps: (1) fixation of the biological structure to be analyzed (e.g., a chromosome spread), (2) pre-hybridization treatment of the biological structure to increase accessibility of target DNA (e.g., denaturation with heat or alkali), (3) optional pre-hybridization treatment to reduce nonspecific binding (e.g., by blocking the hybridization capacity of repetitive sequences), (4) hybridization of the mixture of nucleic acids to the nucleic acid in the biological structure or tissue; (5) post-hybridization washes to remove nucleic acid fragments not bound in the hybridization and (6) detection of the hybridized labelled oligonucleotides (e.g., hybridized Oligopaints). The reagents used in each of these steps and their conditions of use vary depending on the particular situation and whether their use is required with any particular probes. Hybridization conditions are also described in U.S. Pat. No. 5,447,841. It will be appreciated that numerous variations of in situ hybridization protocols and conditions are known and may be used in conjunction with the present invention by practitioners following the guidance provided herein.

Probes included within the scope of the present disclosure include those known to be useful with FISH methods. FISH probes are typically derived from genomic inserts subcloned into vectors such as plasmids, cosmids, and bacterial artificial chromosomes (BACs), or from flow-sorted chromosomes. These inserts and chromosomes can be used to produce probes labeled directly via nick translation or PCR in the presence of fluorophore-conjugated nucleotides or probes labeled indirectly with nucleotide-conjugated haptens, such as biotin and digoxigenin, which can be visualized with secondary detection reagents. Probe DNA is often fragmented into about 150-250 bp pieces to facilitate its penetration into fixed cells and tissues. As many genomic clones contain highly repetitive sequences, such as SINE and Alu elements, hybridization often needs to be performed in the presence of unlabeled repetitive DNA to prevent off-target hybridizations that increase background signal. Such probes may be referred to as "chromosome paints" which refers to detectably labeled polynucleotides that have sequences complementary to DNA sequences from a particular chromosome or sub-chromosomal region of a particular chromosome. Chromosome paints that are commercially available are derived from fluorescence activated cell sorted (FACS) and/or flow sorted chromosomes or from bacterial artificial chromosomes (BACs) or yeast artificial chromosomes (YACs).

Many types of custom-synthesized oligonucleotides (oligos) have also been used as FISH probes, including DNA, peptide nucleic acid (PNA), and locked nucleic acid (LNA) oligos. One advantage of oligo probes is that they are designed to target a precisely defined sequence rather than relying on the isolation of a clone that is specific for the desired genomic target. Also, as these probes are typically short (about 5 bp to about 300 bp, about 8 bp to about 250 bp, about 9 bp to about 200 bp, about 10 bp to about 150 bp, about 15 bp to about 100 bp or about 20 bp to about 50 bp) and single-stranded by nature, they efficiently diffuse into fixed cells and tissues and are unhindered by competitive hybridization between complimentary probe fragments. Recently developed methods utilizing oligo probes have allowed the visualization of single-copy viral DNA as well as individual mRNA molecules using branched DNA signal amplification or a few dozen short oligo probes and, by targeting contiguous blocks of highly repetitive sequences as a strategy to amplify signal, enabled the first FISH-based genome-wide RNAi screen. Oligo FISH probes have also been generated directly from genomic DNA using many parallel PCR reactions or using rolling circle methods, or methods using many rounds of T7 RNA polymerase followed by one or more rounds of reverse transcription (during which label or precursor of the label is added either via the primer or during elongation) and elimination/degradation of the RNA template. Such methods are known to those of skill in the art.

Oligonucleotide sequences, such as single stranded oligonucleotide sequences to be used for probes, may be isolated from natural sources, synthesized or purchased from commercial sources. In certain exemplary embodiments, oligonucleotide sequences may be prepared using one or more of the phosphoramidite linkers and/or sequencing by ligation methods known to those of skill in the art. Oligonucleotide sequences may also be prepared by any suitable method, e.g., standard phosphoramidite methods such as those described herein below as well as those described by Beaucage and Carruthers ((1981) *Tetrahedron Lett.* 22: 1859) or the triester method according to Matteucci et al. (1981) *J. Am. Chem. Soc.* 103:3185), or by other chemical methods using either a commercial automated oligonucleotide synthesizer or high-throughput, high-density array methods known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

In certain exemplary embodiments, oligonucleotide sequences may be prepared using a variety of microarray technologies known in the art. Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) *Proc. Natl. Acad. Sci. U.S.A.* 93:13555; *Synthetic DNA Arrays* In Genetic Engineering, Vol. 20:111, Plenum Press (1998); Duggan et al. (1999) *Nat. Genet.* S21:10; *Microarrays: Making Them and Using Them* In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Application Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597.

Polymerase recognition sites, cleavage sites and/or label or detectable moiety addition sites may be added to the single stranded oligonucleotides during synthesis using known materials and methods.

Oligonucleotide probes useful for probes according to the present disclosure may have any desired nucleotide length and nucleic acid sequence. Accordingly, aspects of the present disclosure are directed to the use of a plurality or set of nucleic acid probes, such as single stranded nucleic acid probes, such as oligonucleotide paints. The term "probe" refers to a single-stranded oligonucleotide sequence that will recognize and form a hydrogen-bonded duplex with a complementary sequence in a target nucleic acid sequence or its cDNA derivative. The probe includes a target hybridizing nucleic acid sequence. Exemplary nucleic acid sequences may be short nucleic acids or long nucleic acids. Exemplary nucleic acid sequences include oligonucleotide paints. Exemplary nucleic acid sequences are those having between about 1 nucleotide to about 100,000 nucleotides, between about 3 nucleotides to about 50,000 nucleotides, between about 5 nucleotides to about 10,000 nucleotides, between about 10 nucleotides to about 10,000 nucleotides, between about 10 nucleotides to about 1,000 nucleotides, between about 10 nucleotides to about 500 nucleotide, between about 10 nucleotides to about 100 nucleotides, between about 10 nucleotides to about 70 nucleotides, between about 15 nucleotides to about 50 nucleotides, between about 20 nucleotides to about 60 nucleotides, between about 50 nucleotides to about 500 nucleotides, between about 70 nucleotides to about 300 nucleotides, between about 100 nucleotides to about 200 nucleotides, and all ranges or values in between whether overlapping or not. Exemplary oligonucleotide probes include between about 10 nucleotides to about 100 nucleotides, between about 10 nucleotides to about 70 nucleotides, between about 15 nucleotides to about 50 nucleotides, between about 20 nucleotides to about 60 nucleotides and all ranges and values in between whether overlapping or not. According to one aspect, oligonucleotide probes according to the present disclosure should be capable of hybridizing to a target nucleic acid. Probes according to the present disclosure may include a label or detectable moiety, or a matrix attachment moiety as described herein. Oligonucleotides or polynucleotides may be designed, if desired, with the aid of a computer program such as, for example, DNAWorks, or Gene2Oligo.

Oligonucleotide probes according to the present disclosure need not form a perfectly matched duplex with the single stranded nucleic acid, though a perfect matched duplex is exemplary. According to one aspect, oligonucleotide probes as described herein form a stable hybrid with that of the target sequence under stringent to moderately stringent hybridization and wash conditions. If it is expected that the probes will be essentially completely complementary (i.e., about 99% or greater) to the target sequence, stringent conditions will be used. If some mismatching is expected, with the result that the probe will not be completely complementary, the stringency of hybridization may be lessened. Conditions which affect hybridization, and which select against nonspecific binding are known in the art, and are described in, for example, Sambrook et al., (2001). Generally, lower salt concentration and higher temperature increase the stringency of binding. For example, it is usually considered that stringent conditions are incubations in solutions which contain approximately 0.1×SSC, 0.1% SDS, at about 65° C. incubation/wash temperature, and moderately stringent conditions are incubations in solutions which contain approximately 1-2×SSC, 0.1% SDS and about 50°-65° C. incubation/wash temperature. Low stringency conditions are 2×SSC and about 30°-50° C.

The terms "stringency" or "stringent hybridization conditions" refer to hybridization conditions that affect the stability of hybrids, e.g., temperature, salt concentration, pH, formamide concentration and the like. These conditions are empirically optimized to maximize specific binding and minimize non-specific binding of primer or probe to its target nucleic acid sequence. The terms as used include reference to exemplary conditions under which a probe or primer will hybridize to its target sequence, to a detectably greater degree than other sequences (e.g. at least 2-fold over background). Other such conditions may be appropriate. Stringent conditions are sequence dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength and pH) at which 50% of a complementary target sequence hybridizes to a perfectly matched probe or primer. Typically, stringent conditions will be those in which the salt concentration is less than about 1.0 M $Na^+$ ion, typically about 0.01 to 1.0 M $Na^+$ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1M NaCl, 1% SDS at 37° C., and a wash in 0.1×SSC at 60° C. Hybridization procedures are well known in the art and are described by e.g. Ausubel et al., 1998 and Sambrook et al., 2001. It is to be understood that any desired stringency and/or conditions may be employed as desired.

Nucleic acid probes according to the present disclosure may be labeled or unlabeled. Certain nucleic acid probes may be directly labeled or indirectly labeled. Certain nucleic acid probes may directly include a matrix attachment moiety. Certain nucleic acid probes may indirectly include a matrix attachment moiety, such as by a secondary oligonucleotide which hybridizes to the probe and wherein the matrix attachment moiety is directly attached to the secondary oligonucleotide.

According to certain aspects, nucleic acid probes may include a primary nucleic acid sequence that is non-hybridizable to a target nucleic acid sequence in addition to the sequence of the probe that hybridizes to the target nucleic acid sequence. Exemplary primary nucleic acid sequences or target non-hybridizing nucleic acid sequences include between about 10 nucleotides to about 100 nucleotides, between about 10 nucleotides to about 70 nucleotides, between about 15 nucleotides to about 50 nucleotides, between about 20 nucleotides to about 60 nucleotides and all ranges and values in between whether overlapping or not. According to certain aspects, the primary nucleic acid sequence is hybridizable with one or more secondary nucleic acid sequences. According to certain aspects, the secondary nucleic acid sequence may include a label or a matrix attachment moiety. According to this aspect, the nucleic acid probes are indirectly labeled or indirectly include a matrix attachment moiety as the secondary nucleic acid binds to the primary nucleic acid thereby indirectly labeling the probe which hybridizes to the target nucleic acid sequence or indirectly providing the probe with the matrix attachment moiety. According to certain aspects, a plurality of nucleic acid probes is provided with each having a common primary nucleic acid sequence. That is, the primary nucleic acid sequence is common to a plurality of nucleic acid probes, such that each nucleic acid probe in the plurality has the same or substantially similar primary nucleic acid sequence. According to one aspect, the primary nucleic acid sequence is a single sequence species. In this manner, a plurality of common secondary nucleic acid sequences is provided which hybridize to the plurality of common primary nucleic acid sequences. That is, each secondary nucleic acid sequence has the same or substantially similar nucleic acid sequence. According to one exemplary embodiment, a single primary nucleic acid sequence is provided for each of the nucleic acid probes in the plurality. Accordingly, only a single secondary nucleic acid sequence which is hybridizable to the primary nucleic acid sequence need be provided to label each of the nucleic acid probes. According to certain aspects, the common secondary nucleic acid sequences may include a common label or common matrix attachment moiety. According to this aspect, a plurality of nucleic acid probes are provided having substantially diverse nucleic acid sequences hybridizable to different target nucleic acid sequences and where the plurality of nucleic acid probes have common primary nucleic acid sequences. Accordingly, a common secondary nucleic acid sequence having a label or attachment moiety may be used to indirectly label or provide an attachment moiety to each of the plurality of nucleic acid probes. According to this aspect, a single or common primary nucleic acid sequence and secondary nucleic acid sequence pair can be used to indirectly label or provide an attachment moiety to diverse nucleic acid probe sequences. Such an embodiment is provided where a plurality of nucleic acid probes having primary nucleic acid sequences are commercially synthesized, such as on an array. Labeled secondary nucleic acid sequences can also be commercially synthesized so that they are hybridizable with the primary nucleic acid sequences. The nucleic acid probes may be combined with the labeled secondary nucleic acids and one or more or a plurality of target nucleic acid sequences under conditions such that the nucleic acid probe or probes hybridize to the target nucleic acid sequence or sequences while the primary nucleic acid sequence is nonhybridizable to the target nucleic acid sequence or sequences. A secondary nucleic acid sequence having a label or attachment moiety hybridizes with a corresponding primary nucleic acid sequence.

According to certain aspects, the primary nucleic acid sequence is modifiable with one or more labels or attachment moieties. According to this aspect, one or more labels or attachment moieties may be added to the primary nucleic acid sequence using methods known to those of skill in the art.

According to an additional embodiment, nucleic acid probes may include a first half of a ligand-ligand binding pair, such as biotin-avidin. Such nucleic acid probes may or may not include a primary nucleic acid sequence. The first half of a ligand-ligand binding pair may be attached directly to the nucleic acid probe. According to certain aspects, a second half of the ligand-ligand binding pair may include a label or attachment moiety or the second half of the ligand-ligand binding pair may be on a target nucleic acid such as a chromosome, to thereby attach the probe to the chromosome.

Complex oligo libraries produced by massively parallel synthesis may be used as probes as described herein. These libraries are synthesized on a solid substrate, then amplified or chemically cleaved in order to move the library into solution. Additional labeled probes include those known as "oligopaints" as described in US 2010/0304994 hereby incorporated by reference in its entirety for all purposes. As used herein, the term "Oligopaint" refers to detectably labeled polynucleotides that have sequences complementary to an oligonucleotide sequence, e.g., a portion of a DNA sequence e.g., a particular chromosome or sub-chromosomal region of a particular chromosome. Oligopaints are generated from synthetic probes and arrays that are, optionally, computationally patterned (rather than using natural DNA sequences and/or chromosomes as a template). Since Oligopaints are generated using nucleic acid sequences that are present in a pool, they are no longer spatially addressable (i.e., no longer attached to an array). Surprisingly, however, this method increases resolution of the oligopaints over chromosome paints that are made using yeast artificial chromosomes (YACs), bacterial artificial chromosomes (BACs), and/or flow sorted chromosomes.

In certain exemplary embodiments, small Oligopaints are provided. As used herein, the term "small Oligopaint" refers to an Oligopaint of between about 5 bases and about 100 bases long, or an Oligopaint of about 5 bases, about 10 bases, about 15 bases, about 20 bases, about 25 bases, about 30 bases, about 35 bases, about 40 bases, about 45 bases, about 50 bases, about 55 bases, about 60 bases, about 65 bases, about 70 bases, about 75 bases, about 80 bases, about 85 bases, about 90 bases, about 95 bases, or about 100 bases. Small Oligopaints can access targets that are not accessible to longer oligonucleotide probes. For example, in certain aspects small Oligopaints can pass into a cell, can pass into a nucleus, and/or can hybridize with targets that are partially bound by one or more proteins, etc. Small Oligopaints are also useful for reducing background, as they can be more easily washed away than larger hybridized oligonucleotide sequences. As used herein, the terms "Oligopainted" and "Oligopainted region" refer to a target nucleotide sequence (e.g., a chromosome) or region of a target nucleotide sequence (e.g., a sub-chromosomal region), respectively, that has hybridized thereto one or more Oligopaints. Oligopaints can include an attachment moiety or linker for attachment to a matrix or a detectable label for use to target a nucleotide sequence with a detectable label, e.g., chromosomes and sub-chromosomal regions of chromosomes during various phases of the cell cycle including, but not limited to, interphase, preprophase, prophase, prometaphase, metaphase, anaphase, telophase and cytokenesis. Oligopaints may be used for diffraction-limited microscopy (often called conventional light microscopy) as well as super-resolution microscopy i.e., Stimulated Emission Depletion Microscopy or STED, Structured Illumination Microscopy or SIM, and single-molecule super-resolution microscopy technologies, such as Photo-Activated Localization Microscopy or PALM, stochastic Optical Reconstruction Microscopy or STORM and DNA-based Point Accumulation In Nanoscale Topography or DNA-PANT, which are known to those of skill in the art.

Methods of Cleaving a Chromosome at a Plurality of Locations

The disclosure provides for a method of attaching a chromosome, or portion or fragment thereof or other naturally occurring nucleic acid to a matrix by cleaving the chromosome or other naturally occurring nucleic acid to produce free ends or terminal nucleotides and then modifying the free ends or terminal nucleotides to include matrix attachment moieties. The disclosure provides for site specific cleavage using methods known to those of skill in the art. After chromosome cleavage or breakage, two or more chromosomal fragments are produced. Each of these fragments may have a fractured extremity referred to as an overhang. These broken ends appear sticky and have the ability to adhere to another such sticky end, which provides a method for attaching a nucleotide or oligonucleotide including a matrix attachment moiety to the fragment. The fragments may also have blunt ends to which a nucleotide or oligonucleotide including a matrix attachment moiety can be attach directly or after modification of the blunt end to produce an overhang.

The chromosome or other naturally occurring nucleic acid may be placed within a matrix so as to maintain the three-dimensional structure of the chromosome and its relative location within a cell and may be cleaved, for example using site specific cleavage enzymes or methods, to produce free ends or terminal nucleotides using methods known to those of skill in the art. Exemplary cleavage enzymes include those that cleave a single strand (nicking nucleases) of a double stranded nucleic acid or those that cleave both strands of a double stranded nucleic acid.

The disclosure contemplates use of a restriction enzyme or restriction endonuclease which is an enzyme that cuts DNA at or near specific recognition nucleotide sequences known as restriction sites. Restriction enzymes are commonly classified into three types, which differ in their structure and whether they cut their DNA substrate at their recognition site, or if the recognition and cleavage sites are separate from one another. To cut DNA, restriction enzymes make two incisions, once through each sugar-phosphate backbone (i.e. each strand) of the DNA double helix. Restriction enzymes are readily identifiable in the literature and are commercially available. Naturally occurring restriction endonucleases are categorized into four groups (Types I, II III, and IV) based on their composition and enzyme cofactor requirements, the nature of their target sequence, and the position of their DNA cleavage site relative to the target sequence. Many enzymes recognize specific short DNA sequences and carry out the endonucleolytic cleavage of DNA to give specific fragments with terminal 5'-phosphates. They differ in their recognition sequence, subunit composition, cleavage position, and cofactor requirements.

Type I enzymes cleave at sites remote from recognition site; require both ATP and S-adenosyl-L-methionine to function; multifunctional protein with both restriction and methylase activities. Type II enzymes cleave within or at short specific distances from recognition site; most require magnesium; single function (restriction) enzymes independent of methylase. Type III enzymes cleave at sites a short distance from recognition site; require ATP (but do not hydrolyse it); S-adenosyl-L-methionine stimulates reaction but is not required; and exist as part of a complex with a modification methylase. Type IV enzymes target modified DNA, e.g. methylated, hydroxymethylated and glucosyl-hydroxymethylated DNA. Type V restriction enzymes (e.g., the cas9-gRNA complex from CRISPRs) utilize guide RNAs to target specific non-palindromic sequences found on invading organisms. They can cut DNA of variable length, provided that a suitable guide RNA is provided. Artificial restriction enzymes can be generated by fusing a natural or engineered DNA binding domain to a nuclease domain (often the cleavage domain of the type IIS restriction enzyme FokI.) Such artificial restriction enzymes can target large DNA sites (up to 36 bp) and can be engineered to bind to desired DNA sequences. Zinc finger nucleases are the most commonly used artificial restriction enzymes and are generally used in genetic engineering applications, but can also be used for more standard gene cloning applications. Other artificial restriction enzymes are based on the DNA binding domain of TAL effectors, such as TALENS. Exemplary restriction enzymes include EcoRI, EcoRII, BamHI, HindIII, TaqI, NotI, HinFI, Sau3AI, PvuII, SmaI, HaeIII, HgaI, AluI, EcoRV, EcoP15I, KpnI, PstI, SacI, SalI, ScaI, SpeI, SphI, StuI, and XbaI. The use of restriction endonucleases to cleave DNA is described in Kejnovsky et al., International Journal of Biological Macromolecules 34 (2004) 213-222 hereby incorporated by reference in its entirety.

The disclosure contemplates use of a deoxyribonuclease (Dnase) which may be used to catalyze the hydrolytic cleavage of phosphodiester linkages in a DNA backbone thereby cleaving a nucleic acid such as DNA or a chromosome. A wide variety of deoxyribonucleases, whether exonucleases or endonucleases, are known in the art, and which differ in their substrate specificities, chemical mechanisms, and biological functions. An exemplary Dnase is Dnase I or Dnase II.

The disclosure contemplates other methods known in the art to cleave or cut DNA such as UV irradiation or ionizing irradiation. If ionizing radiation interacts with a DNA macromolecule, the energy transferred can rupture one of its chemical bonds, possibly severing one (single stranded break) or two (double stranded break) of the sugar-phosphate bonds.

Methods of Connecting a Nucleotide or Oligonucleotide to a Free End Terminal Nucleotide The disclosure provides the addition of a nucleotide or oligonucleotide to a free end terminal nucleotide using methods known to those of skill in the art, such as ligation, extension and the like. In general, ligation can be accomplished either enzymatically or chemically. "Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. Such ligases include DNA ligases known to those of skill in the art and RNA ligases known to those of skill in the art. DNA ligases include bacterial and mammalian DNA ligases. Exemplary ligases include T3 ligase, T4 ligase, T7 ligase, E. coli DNA ligase, Taq DNA ligase, circ-ligase and the like. A variety of template-driven ligation reactions are described in the following references: Whitely et al., U.S. Pat. No. 4,883,750; Letsinger et al., U.S. Pat. No. 5,476,930; Fung et al., U.S. Pat. No. 5,593,826; Kool, U.S. Pat. No. 5,426,180; Landegren et al., U.S. Pat. No. 5,871,921; Xu and Kool (1999) *Nucl. Acids Res.* 27:875; Higgins et al., *Meth. in Enzymol.* (1979) 68:50; Engler et al. (1982) *The Enzymes,* 15:3 (1982); and Namsaraev, U.S. Patent Pub. 2004/0110213. Chemical ligation methods are disclosed in Ferris et al., Nucleosides & Nucleotides, 8: 407-414 (1989) and Shabarova et al., Nucleic Acids research, 19: 4247-4251 (1991). Enzymatic ligation utilizes a ligase. Many ligases are known to those of skill in the art as referenced in Lehman, Science, 186: 790-797 (1974); Engler et al., DNA ligases, pages 3-30 in Boyer, editor, The Enzymes, Vol. 15B (Academic Press, New York, 1982); and the like. Exemplary ligases include T4 DNA ligase, T7 DNA ligase, E. coli DNA ligase, Taq ligase, Pfu ligase and the like. Certain protocols for using ligases are disclosed by the manufacturer and also in Sambrook, Molecular Cloning: A Laboratory manual, $2^{nd}$ Edition (Cold Spring Harbor Laboratory, New York, 1989); Barany, PCR Methods and Applications, 1:5-16 (1991); Marsh et al., Strategies, 5:73-76 (1992).

Nucleotides may also be added to a free end terminal nucleotide by polymerases. Polymerases are enzymes that produce a nucleic acid sequence. Such polymerases may be template dependent or template independent. Polymerases that produce RNA polymers are known as RNA polymerases, while polymerases that produce DNA polymers are known as DNA polymerases. Exemplary DNA polymerases include DNA polymerase I, DNA polymerase II, DNA polymerase III, DNA polymerase IV, DNA polymerase V and the like. DNA polymerases are well known to those of skill in the art. Exemplary RNA polymerases include RNA polymerase, RNA polymerase II, RNA polymerase III, T7 RNA polymerase and the like. RNA polymerases are well known to those of skill in the art.

Polymerases that incorporate errors are known in the art and are referred to herein as an "error-prone polymerases". Template independent polymerases may be error prone polymerases. Template-independent polymerases such as terminal deoxynucleotidyl transferase (TdT), also known as DNA nucleotidylexotransferase (DNTT) or terminal transferase create nucleic acid strands by catalyzing the addition of nucleotides to the 3' terminus of a DNA molecule without a template. Further description of TdT is provided in *Biochim Biophys Acta.*, May 2010; 1804(5): 1151-1166 hereby incorporated by reference in its entirety.

The modified nucleotides may be added during synthesis. Synthesis may refer by example to solid support synthesis of oligonucleotides. In this case, modified nucleic acids, which can be a nucleic acid analog, or a nucleic acid modified with a matrix attachment moiety, are to the nucleic acid fragments. Synthesis may also refer to the process performed by a polymerase while it synthesizes the complementary strands of a nucleic acid template. Certain DNA polymerases are capable of using and incorporating nucleic acids analogs, or modified nucleic acids, modified with a matrix attachment moiety to the complementary nucleic acid template.

A nucleotide may be indirectly added to a free end terminal nucleotide by hybridization of an oligonucleotide containing the nucleotide to an overhang or by creating an overhang such as by ligation and hybridization of an oligonucleotide containing the nucleotide. Alternatively, an attachment moiety may be used to attach a first oligonucleotide to the free end terminal nucleotide and a complementary oligonucleotide including the matrix attachment moiety may be hybridized to the first oligonucleotide. Methods of indirectly adding a label or attachment moiety are described herein.

Example I

Oligopaints are Sequenced Using FISSEQ within an Expanded Matrix

Figure 2:
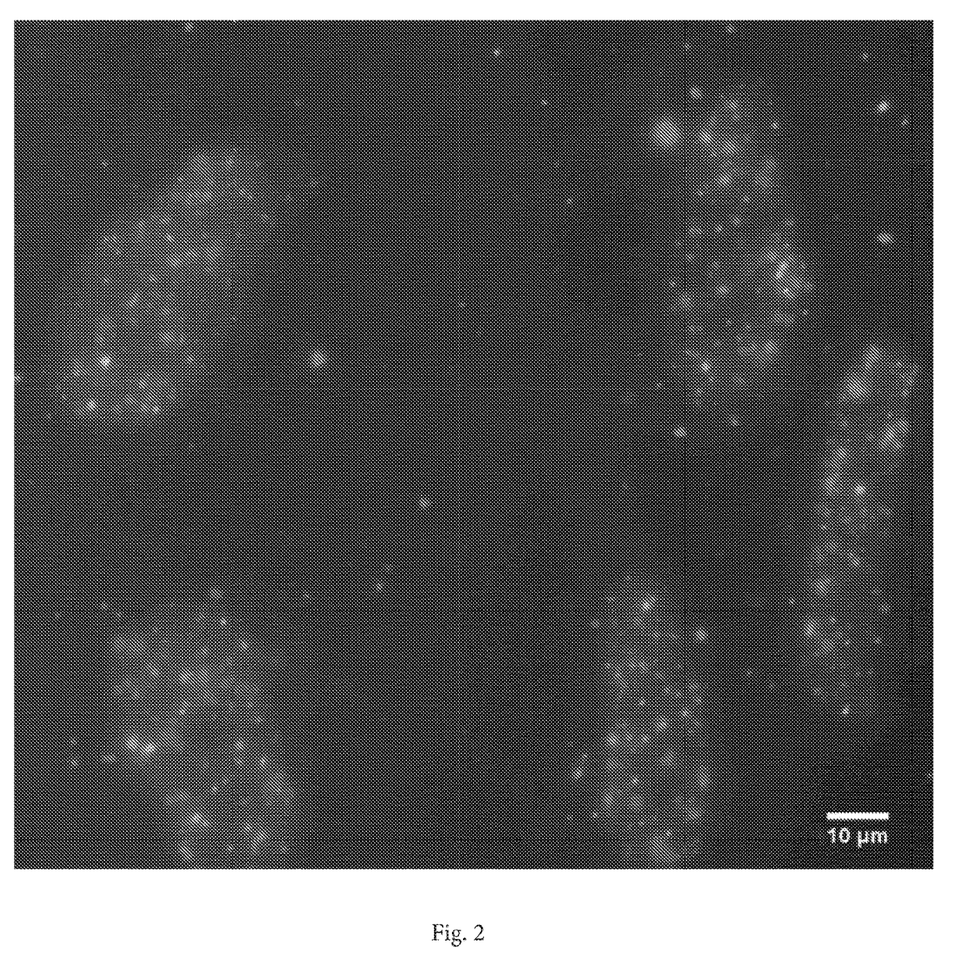
FIG. 2 is an image of cells with an expandable matrix having undergone in situ genome sequencing. IMR90 cells were stained with Oligopaints targeting 300 Kb-1 Mb unique regions on each chromosome with 3750 Oligopaints per region (~8 probes/Kb). Cells were then expanded ~4.5× in ExM gel. Oligopaint circularization, followed by Rolling Circle Amplification, and 1 round of sequencing by ligation was performed. Various colors represent 1 base of SoliD sequencing. Scale bar=10 microns.

PGP1F cells were plated onto glass microscope slides and were allowed to adhere overnight at 37° C. in a cell culture incubator. On the next day, cells on slides were transferred to coplin jars and washed 1× with 1×PBS, followed by fixation with 4% formaldehyde in PBS for 10 min at RT (room temperature). Another 1×PBS wash was performed and cells were permeabalized in 1×PBS+0.5% Triton X-100 for 10 min at RT. Two 1×PBS+0.1% Triton X-100 (1×PBT) washes for 5 minutes were performed at RT for 5 min each. Slides could then be stored in 1×PBT at 4° C. or be used for experiments. If proceeding to experiments, slides were treated in 0.1N HCl for 5 min at RT. Two washes in 2×SSCTween for 5 min at RT were performed. Next, pre-hybridization was done in 50% formamide in 2×SSCT solution for 5 min at RT. Another wash in same buffer was done at 60° C. for 20 min. Slides were slightly air-dried and 25 uL of probe solution including 100 pmols of Oligopaints in 50% formamide, 10% Polyacrylic Acid, 2×SSCT, and 20 mg RNAse1 were added to each slide, covered with a 22×22 mm cover slip and sealed with rubber cement. Probes were hybridized O/N at 42° C. in a humid chamber. The next day, rubber cement and coverslips were carefully removed. Unbound probes were washed off with 2×SSCT at 60° C. for 20 min. 2× 2×SSCT washes were performed at RT for 5 min each, followed by 0.2×SSC wash for 5 min at RT. 30 uL of ExM gel was cast over cells on slide using gelation chamber (parafilm wrapped glass microscope slide with 2 22×22 1.5 coverslips used as spacers) and allowed to polymerize at 37° C. for 1 hr. After polymerization, gelation chamber was carefully removed and gels on slide were digested O/N in digestion buffer and 1:100 of NEB Proteinase K (20 mg/mL) at 37° C. Following digestion, glass slides were removed and gels were expanded in 1×PBS by shaking 2× for 7 min at RT. To ensure that gels remained expanded during subsequent steps, gels were re-embedded. Gels were tilted in 1.5 mL tube with 3% Acrylamide/BIS in 1×PBS with 0.05% APS and 0.05% TEMED for 20 min at RT. Gels were then removed and placed on microscope slide. A piece of 1.5 coverslip, broken to be big enough to cover the gel, was placed over the gel. Covered gels on microscope slide were placed in humid chamber that was filled with Argon gas to remove oxygen from chamber. Gelling proceeded at 37° C. for 1 hr. Re-embedded gels were washed 1× for 7 min in 100 mM MES at RT. Samples were passivated for 2 hrs at RT in 150 mM EDC, 150 mM NHS, 2M Ethanolamine hydrochloride, and 5M NaCl. Ethanolamine was then reacted for 40 min at RT by adding 2M Ethanolamine hydrochloride, 62.5 mM Sodium Borate Buffer (pH 8.5), and 5M NaCl to gels. Gels were then washed 3× in 1× SoLiD Instrument Buffer for 10 min at RT. Wash in 1× T4 Ligase Buffer for 7 min at RT was done to prepare for Oligopaint circularization. Oligopaints were then circularized by adding 2 uM Oligo Splint in 1× T4 Ligase Buffer and T4 DNA Ligase for 2 hrs at RT with gentle shaking. Samples were then washed 2× in 1× Instrument buffer for 7 min at RT, followed by washing in 1×NEB Buffer 1 for 7 min at RT. ssDNA and non-circularized Oligopaints were degraded by 1 uL NEB Exonuclease I in 1× Exonuclease I Buffer for 45 min at 37° C. 3× 1× instrument buffer washes for 7 min at RT, then 1× 10 min wash in 30% formamide in 2×SSC at RT. Hybridization of 1 uM Rolling Circle Amplification (RCA) primer (same as Splint) was done in 30% formamide and 2×SSC for 1 hr at RT. After RCA primer hybridization, samples were washed 2× 10 min in instrument buffer followed by 1× 10 min in Phi29 Polymerase Buffer. RCA was performed by adding 1× Phi29 buffer, 250 uM dNTPs, 20 uM aminoallyl dUTP, and 2 Units of Phi29 DNA polymerase O/N at 30° C. RCA amplicons were crosslinked for 30 min at RT in 20 uL BS(PEG)9 in 980 uL 1×PBS. Quenching of BS(PEG)9 was done by incubating samples in 1M Tris (pH 8.0) for 45 min. Quenched samples were then washed 3× 10 min in 1× instrument buffer at RT. To prepare for sequencing, 2.5 uM sequencing primer in 5×SSCT was hybridized for 1 hr at RT. 2× 10 min washes in 1× instrument buffer was done, followed by washing in 1× T4 DNA ligase buffer for 10 min at RT. To sequence, 1× T4 ligation buffer, 5 uL of T4 DNA ligase, 1 uL of SoLiD sequencing nucleotide mix, with 84 uL of water was added to each sample for 2 hrs at RT. Samples were then washed with 1× instrument buffer for 1 hr at RT before imaging. FIG. 2 shows that Oligopaint circularization, followed by Rolling Circle Amplification, and 1 round of SoLiD sequencing by ligation is achieved in-situ, in fixed and expanded human cells.

Example II

Figure 3A:
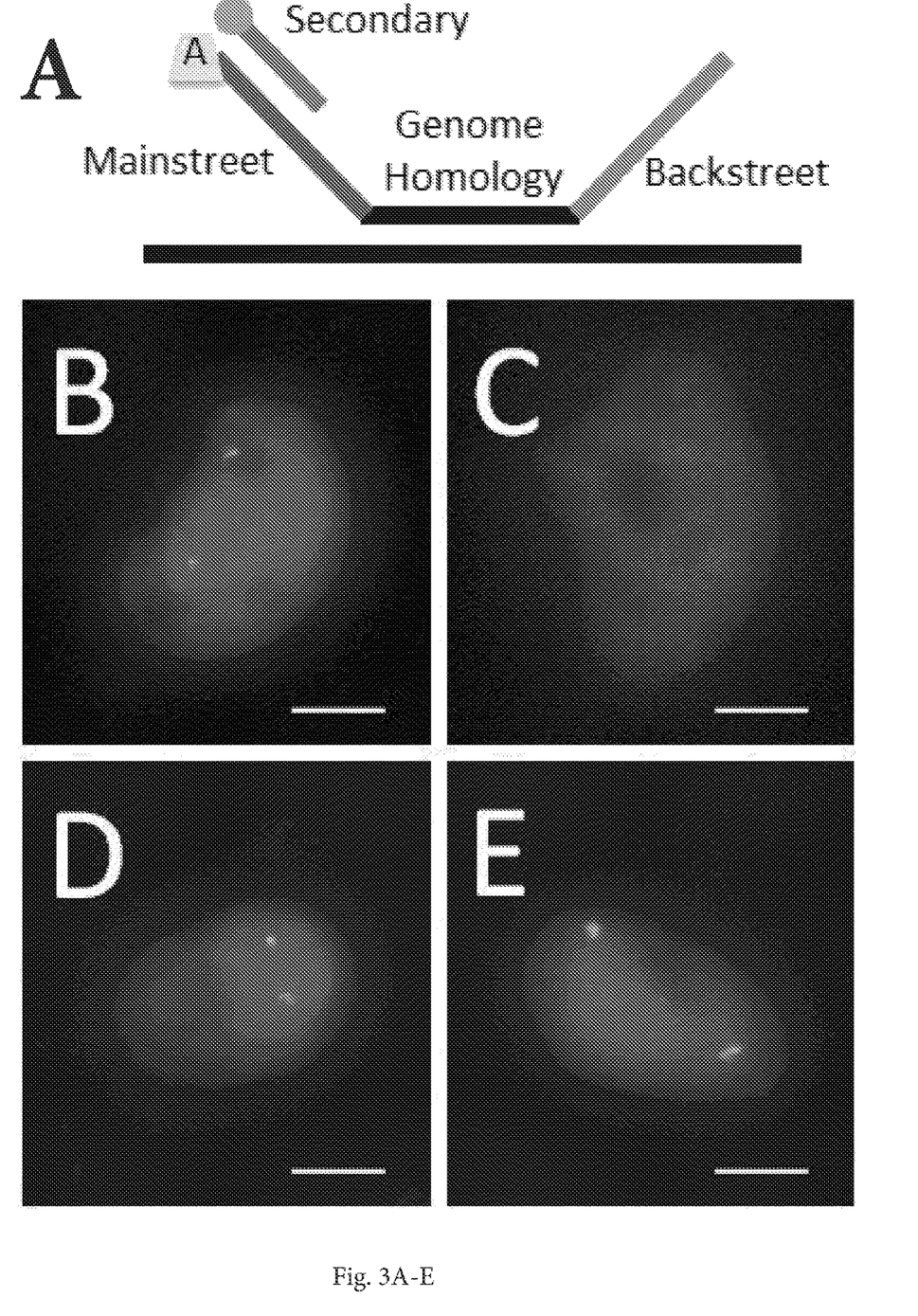
FIG. 3A is a schematic depicting Oligopaint with Acrydite modification. Acrydite (Yellow trapezoid) is incorporated onto the 5' end of each Oligopaint. Oligopaints are visualized with a fluorophore labeled secondary oligo binding to the Mainstreet (non-genomic sequence upstream of the complementary nucleic acid sequence.

Oligopaints with an Acrydite Attachment Moiety are Attached to a Matrix and Hybridized with a Secondary Oligo Bearing a Detectable Moiety Oligopaint library was first PCR amplified linearly to limit PCR errors. PCR product was column purified and resuspended in water. This linear product was PCR amplified again and T7 promoter sequences were added to each backstreet (non-genomic sequence downstream of the complementary sequence) via reverse primer. 1.3 ug of purified PCR products were in-vitro transcribed O/N at 37° C. This RNA served as the template for reverse transcription using forward primers containing 5' Acrydite modification to append Acrydite to Oligopaint. RNA was degraded by alkaline hydrolysis. Samples were then purified with Zymo 100 column purification kit, using Oligobinding Buffer instead of DNA binding buffer. Acrydite modified oligopaints were then used in standard FISH protocol. Following O/N hybridization of Acrydite modified Oligopaints, ExM (expandable matrix) gel was cast over samples using gelation chamber and allowed to polymerize at 37° C. for 1 hr. Gels were digested O/N in digestion buffer with 1:100 Proteinase K (NEB). Gels were washed 3× 30 min in 2×SSCT. Gels were then cut and separated such that some samples could be probed with secondary oligo (Sample N) and some could be denatured prior to probing with secondary probe (Sample D) to assess tethering to ExM gel matrix. Sample N were kept in 2×SSCT at RT. Sample D were incubated in 70% formamide/2×SSC at 73° C. for 3 min 2× to confirm tethering of Acrydite modified Oligopaint to matrix. Sample D was then washed with 2×SSCT 2× for 10 min at RT. 3.3 uM secondary oligos were hybridized to Sample N and D for 1 hr at RT. Gels were washed in 30% formamide in 2×SSCT for 2× at RT for 30 min. 2 washes in 2×SSCT for 10 min were performed, followed by 1:500 DAPI in PBS staining for 20 min at RT. Samples were then imaged. FIG. 3A-3E are directed to the successful synthesis of Oligopaints with an Acrydite modification at the 5' end as the Oligopaints remain tethered and are able to be hybridized by a secondary oligo after treatment with high concentration of formamide with heating (FIG. 3E). This is in contrast to non-modified Oligopaints that are no longer present in the sample.

The contents of all references, patents and published patent applications cited throughout this application are hereby incorporated by reference in their entirety for all purposes.

EQUIVALENTS

Other embodiments will be evident to those of skill in the art. It should be understood that the foregoing description is provided for clarity only and is merely exemplary. The spirit and scope of the present invention are not limited to the above example, but are encompassed by the claims. All publications, patents and patent applications cited above are incorporated by reference herein in their entirety for all purposes to the same extent as if each individual publication or patent application were specifically indicated to be so incorporated by reference.

What is claimed is:

1. A method of covalently attaching a chromosome within a cell to a matrix comprising
    modifying a plurality of nucleotides within the chromosome to include a matrix attachment moiety wherein the chromosome contacts the matrix, and
    attaching the matrix attachment moiety of the plurality of nucleotides to the matrix, thereby attaching the chromosome to the matrix.

2. The method of claim 1 wherein a matrix-forming material is introduced into the cell and forms the matrix contacting the chromosome.

3. The method of claim 2 wherein the matrix-forming material is polymerized to form the matrix.

4. The method of claim 2 wherein the matrix-forming material is crosslinked to form the matrix.

5. The method of claim 2 wherein the matrix is one or more of polyacrylamide, cellulose, alginate, polyamide, crosslinked agarose, cross-linked dextran, or cross-linked polyethylene glycol.

6. The method of claim 1 wherein the matrix is expanded and additional nucleotides within the chromosome are modified to include a matrix attachment moiety and the matrix attachment moiety is attached to the matrix.

7. The method of claim 1 wherein the matrix is expanded one or more times.

8. The method of claim 1 wherein the matrix is repeatedly expanded.

9. The method of claim 1 wherein the matrix is expanded one or more times, and with each expansion, additional nucleotides within the chromosome are modified to include a matrix attachment moiety and the matrix attachment moiety is attached to the matrix.

10. The method of claim 1 wherein the matrix is repeatedly expanded, and with each expansion, additional nucleotides within the chromosome are modified to include a matrix attachment moiety and the matrix attachment moiety is attached to the matrix.

11. The method of claim 1 wherein the plurality of nucleotides are chemically modified to include the matrix attachment moiety.

12. The method of claim 1 wherein the plurality of nucleotides are chemically modified to include a binding site for a matrix attachment moiety directly or through a linker, and the matrix attachment moiety or the linker is bound to the binding site.

13. The method of claim 1 wherein the plurality of nucleotides are modified by being cleaved from an adjacent nucleotide to produce one or more free end terminal nucleotides, and
    wherein a nucleotide including a matrix attachment moiety is connected directly or as part of an oligonucleotide to the one or more free end terminal nucleotides, and
    the matrix attachment moiety is attached to the matrix.

14. The method of claim 13 wherein the one or more free end terminal nucleotides are processed to allow attachment of the nucleotide including a matrix attachment moiety or the oligonucleotide including the nucleotide including a matrix attachment moiety.

15. The method of claim 13 wherein the one or more free end terminal nucleotides are processed to create blunt ends to allow attachment of the nucleotide including a matrix attachment moiety or the oligonucleotide including the nucleotide including a matrix attachment moiety.

16. The method of claim 13 wherein the one or more free end terminal nucleotides are processed to create overhangs to allow attachment of the nucleotide including a matrix attachment moiety or the oligonucleotide including the nucleotide including a matrix attachment moiety.

17. The method of claim 13 wherein the chromosome is cleaved by a restriction enzyme, a DNase, a single strand cutter, a double strand cutter, or irradiation to create a plurality single stranded or double stranded breaks or gaps.

18. The method of claim 13 wherein the nucleotide including a matrix attachment moiety is ligated directly or via an oligonucleotide to the one or more free end terminal nucleotides.

19. The method of claim 13 wherein the nucleotide including a matrix attachment moiety is extended from the one or more free end terminal nucleotides.

20. The method of claim 13 wherein one or more modified nucleotides are added to a terminal nucleotide using a polymerase,
    attaching a matrix attachment moiety to the one or more modified nucleotides, and
    attaching the matrix attachment moiety to the matrix.

21. The method of claim 13 wherein one or more nucleotides are added to a terminal nucleotide using a polymerase,
    wherein the one or more nucleotides are chemically modified to include a binding site for a matrix attachment moiety directly or through a linker, and
    the matrix attachment moiety or the linker is bound to the binding site, and
    the matrix attachment moiety is attached to the matrix.

22. The method of claim 1 wherein the matrix attachment moiety is a member selected from the group consisting of amine, amine reactive groups, acrydite, an acrydite modified entity, alkyne, biotin, azide, thiol, a thiol-modified entity, and entities suitable for click chemistry techniques.

23. The method of claim 1 wherein the matrix material is expanded in three dimensions creating breaks in chromosomal DNA producing one or more additional free end terminal nucleotides.

24. The method of claim 23 wherein a nucleotide including a matrix attachment moiety is connected directly or indirectly to the one or more additional free end terminal nucleotides, and
    the matrix attachment moiety is attached to the matrix.

25. The method of claim 24 wherein the matrix attachment moiety is a member selected from the group consisting of amine, amine reactive groups, acrydite, an acrydite modified entity, alkyne, biotin, azide, thiol, a thiol-modified entity, and entities suitable for click chemistry techniques.

26. The method of claim 23 wherein the one or more additional free end terminal nucleotides are processed to allow attachment of a nucleotide including a matrix attachment moiety or an oligonucleotide including the nucleotide including a matrix attachment moiety.

27. The method of claim 23 wherein the one or more additional free end terminal nucleotides are processed to create blunt ends to allow attachment of a nucleotide including a matrix attachment moiety or an oligonucleotide including the nucleotide including a matrix attachment moiety.

28. The method of claim 23 wherein the one or more additional free end terminal nucleotides are processed to create overhangs to allow attachment of a nucleotide including a matrix attachment moiety or an oligonucleotide including the nucleotide including a matrix attachment moiety.

29. The method of claim 23 wherein a nucleotide including a matrix attachment moiety is ligated directly or via an oligonucleotide to the one or more additional free end terminal nucleotides.

30. The method of claim 23 wherein a nucleotide including a matrix attachment moiety is extended from the one or more additional free end terminal nucleotides.

31. The method of claim 23 wherein one or more modified nucleotides are added to the one or more additional free end terminal nucleotides using a polymerase, attaching a plurality of matrix attachment moieties to the one or more modified nucleotides, and attaching the matrix attachment moieties to the matrix.

32. The method of claim 23 wherein one or more nucleotides are added to the one or more additional free end terminal nucleotides using a polymerase, wherein the one or more nucleotides are chemically modified to include a binding site for a matrix attachment moiety directly or through a linker, and the matrix attachment moiety or the linker is bound to the binding site, and the matrix attachment moiety is attached to the matrix.

* * * * *